US011801189B2

(12) United States Patent
Larkin et al.

(10) Patent No.: US 11,801,189 B2
(45) Date of Patent: Oct. 31, 2023

(54) ARTICLE OF MANUFACTURE, PATIENT PAD SYSTEM AND METHOD FOR A SURGICAL PROCEDURE

(71) Applicant: Innovative Medical Products, Inc., Plainville, CT (US)

(72) Inventors: Richard M. Larkin, Collinsville, CT (US); Logan S. Sloan, Harwinton, CT (US)

(73) Assignee: Innovative Medical Products, Inc., Plainville, CT (US)

( * ) Notice: Subject to any disclaimer, the term of this patent is extended or adjusted under 35 U.S.C. 154(b) by 719 days.

(21) Appl. No.: 16/986,170

(22) Filed: Aug. 5, 2020

(65) Prior Publication Data

US 2020/0360216 A1     Nov. 19, 2020

Related U.S. Application Data

(63) Continuation-in-part of application No. 15/050,290, filed on Feb. 22, 2016, now Pat. No. 11,510,836.

(51) Int. Cl.
*A61G 13/12* (2006.01)
*A61B 46/20* (2016.01)

(52) U.S. Cl.
CPC ............ *A61G 13/127* (2013.01); *A61B 46/20* (2016.02); *A61G 13/128* (2013.01); *A61B 2046/205* (2016.02)

(58) Field of Classification Search
CPC .............. A61G 13/1235; A61G 13/123; A61G 13/124; A61G 12/125; A61G 13/04;

(Continued)

(56) References Cited

U.S. PATENT DOCUMENTS 4,725,270 A    2/1988  Schuldt et al.
4,907,306 A *  3/1990  Nakaji .................... A47G 9/10
                                              5/640

(Continued)

FOREIGN PATENT DOCUMENTS

WO    WO2013106426 A2    7/2013

OTHER PUBLICATIONS

Innovative Medical Products, Inc., Humbles LapWrap Positioning Pad, Brochure, Aug. 2014, p. 1, Plainville, CT.

(Continued)

*Primary Examiner* — Camtu T Nguyen
(74) *Attorney, Agent, or Firm* — Wasserbauer IP Law; Damian G. Wasserbauer; Nicholas Edward Blanton

(57) ABSTRACT

The invention is a patient positioner assembly, system, article of manufacture, kit, and method of a positioning a patient useful in surgical procedures to secure and hold a patient on a support table. The patient positioner comprises a sheet assembly, a pad assembly, a film for protecting a patient-facing surface of the pad assembly, and straps for a patient's limb(s) that operably connects to a support table pad having hook portions configured to operably connect to a loop base of the sheet assembly thereby operably connecting the support table pad to the sheet assembly. The sheet assembly can be configured as a cover, sheet and/or drape from suitable materials impermeable or that otherwise do not permit the passage of a fluid through its substance to the table pad and/or the split-pad assembly.

10 Claims, 12 Drawing Sheets

(58) Field of Classification Search
CPC .. A61G 13/127; A61G 7/1023; A61G 7/1026; A61G 7/1051; A61G 7/10; A61G 13/1285; A61G 13/128; A61G 13/129; A47C 27/085; A47C 27/146; A61F 5/3761; A61F 5/3769; A61F 5/485; A61B 46/20; A61B 2046/205

See application file for complete search history.

(56) References Cited

U.S. PATENT DOCUMENTS

| | | | |
|---|---|---|---|
| 5,088,137 A | 2/1992 | Rose | |
| 7,287,289 B1* | 10/2007 | Hagopian | A61G 13/08 5/691 |
| 8,464,720 B1 | 6/2013 | Pigazzi et al. | |
| 8,511,314 B2 | 8/2013 | Pigazzi et al. | |
| 8,984,681 B2* | 3/2015 | Ponsi | A61G 7/1026 5/81.1 R |
| 9,125,758 B2* | 9/2015 | Skreosen | A61F 13/15756 |
| 9,161,876 B2 | 10/2015 | Pigazzi et al. | |
| 9,375,343 B2* | 6/2016 | Marshall | A61G 13/1225 |
| 10,842,574 B2 | 11/2020 | Kaforey | |
| 2007/0078419 A1* | 4/2007 | Bredfeldt | A61F 5/485 604/357 |
| 2011/0296609 A1 | 12/2011 | Giap | |
| 2012/0247483 A1* | 10/2012 | Flynn | A61B 18/20 128/845 |
| 2014/0352072 A1 | 12/2014 | Holladay | |
| 2015/0064416 A1* | 3/2015 | Wolf | A61F 13/56 156/226 |
| 2015/0245970 A1 | 9/2015 | Pigazzi et al. | |

OTHER PUBLICATIONS

Innovative Medical Products, Inc., Humbles LapWrap Positioning Pad—Instructions for Use, Brochure, Aug. 2014, p. 1-2, Plainville, CT.

Innovative Medical Products, Inc., Humbles LapWrap Positioning Pad—Extensions, Brochure, Aug. 2014, p. 1, Plainville, CT.

* cited by examiner

ARTICLE OF MANUFACTURE, PATIENT PAD SYSTEM AND METHOD FOR A SURGICAL PROCEDURE

CROSS-REFERENCE TO RELATED APPLICATION

This application claims the benefit of U.S. application Ser. No. 15/050,290 entitled "PAD ASSEMBLY, SYSTEM, METHOD OF PRE-LOAD POSITIONING OF PATIENT FOR MEDICAL PROCEDURE AND KIT" filed on Feb. 22, 2016, which is incorporated herein by reference in its entirety.

FIELD OF THE INVENTION

The present invention relates to a pad assembly, system, kit, and method for maintaining a patient's position during a medical procedure on a support table and, more particularly, to a surgical patient positioner pad system secures and holds the body of the patient in Trendelenburg, reverse Trendelenburg, and/or Fowler's position during a surgical procedure.

BACKGROUND OF THE INVENTION

Conventional patient positioner systems for surgical procedures that incline the support table may injury nerves, skin and other trauma to the patient, e.g. in Trendelenburg, reverse Trendelenburg, and/or other positions. Table inclinations straps are used across the patient's chest to restrain the torso of the patient; however, straps have disadvantages in obstructing ventilation and breathing and may cause pressure injury to nerves, skin, and other trauma injurious to the patient. A headrest may further be used in conjunction with conventional positioning system at additional cost to the patient positioning product.

Conventional Trendelenburg positioner systems also may use a foam pad that contours to the body (e.g. foam, closed-cell foam, memory foam) and straps prevent patient sliding thereby increasing the cost of manufacture and medical waste. Certain pad constructions can have disadvantages by not draining fluids that can lead to further complications such as trap moisture which can place patients at risk for skin maceration, skin tears, bed sore, pressure ulcer, decubitis ulcer and other hospital-acquired pressure injuries (HAPIs). Conventional Trendelenburg positioning pad systems have further disadvantages due to numerosity of parts, sterility, comfort, disposability, waste generated per procedure, and associated manufacturing costs. Consequently, there is a long-felt need for a positioner system for a support table with a lower cost and simplified construction utilizing a disposable drape that operably connects to a patient to the support table pad and a pad assembly with fluid channels for holding the patient during surgical procedures.

SUMMARY OF THE INVENTION

It is an object of the present invention to provide an apparatus, system and method to secure a patient on a support table in a desired position that is maintained throughout the duration of the surgical procedure.

It is an object of the present invention to provide a reusable article of manufacture of a support table pad, for operably connecting to a patient positioning system that maintains a patient in a desired position on the support table.

It is an object of the present invention to provide an article of manufacture of a drape and/or sheet, for operably connecting to the support table pad to a patient positioning system that maintains a patient in a desired position on the support table.

It is an object of the present invention to provide an article of manufacture of a patient positioning system having a patient pad having a loop fabric and/or loop foam for operably connecting to hook portions on a drape or sheet that operably connects to a support table pad to maintain a patient in a desired position on the support table.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Description of the Embodiments, which is to be read in association with the accompanying drawings, which are incorporated in and constitute a part of this specification, show certain aspects of the subject matter disclosed herein and, together with the description, help explain some of the principles associated with the disclosed implementations, wherein.

DESCRIPTION OF THE EMBODIMENTS

Figure 1:
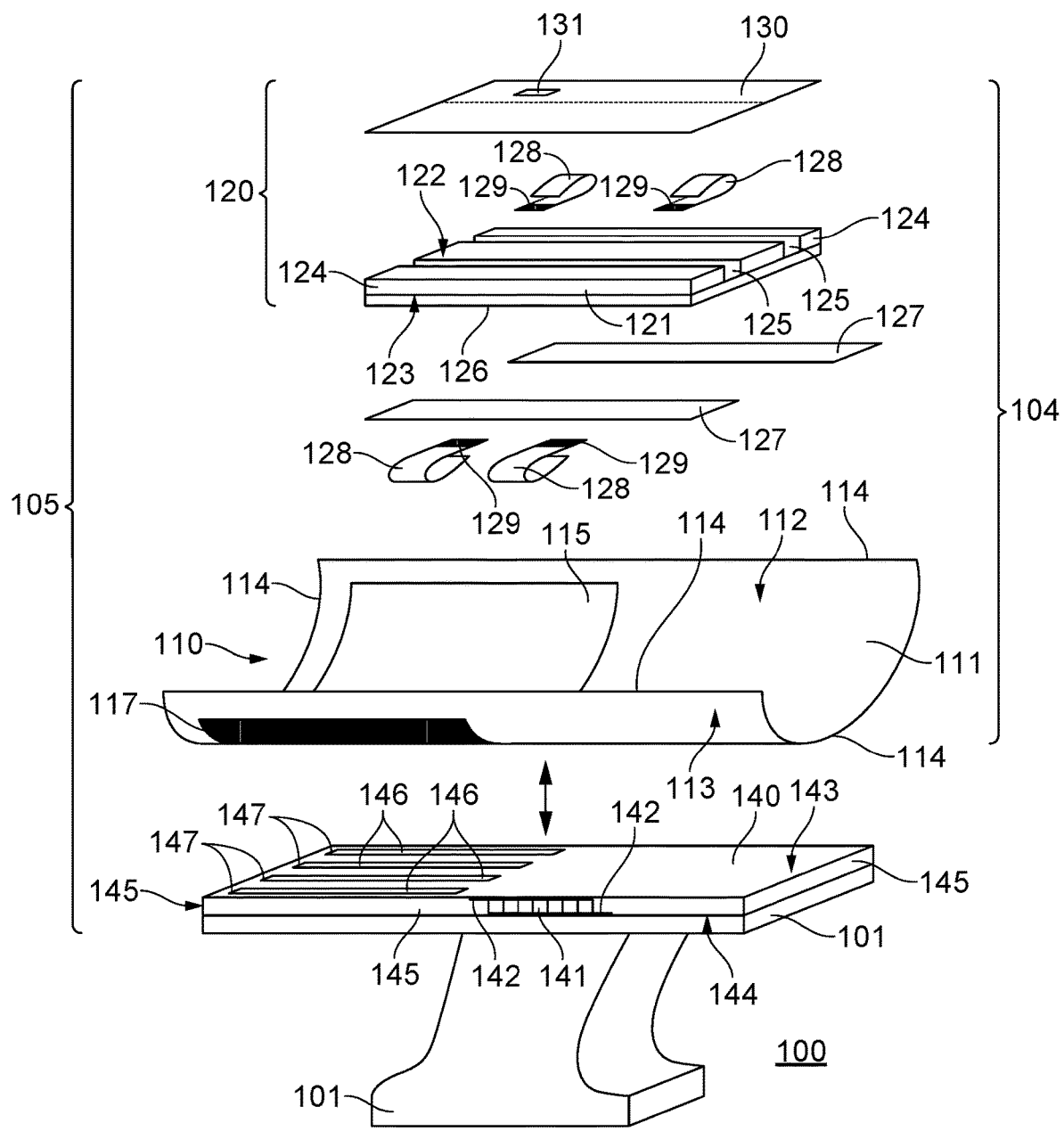
FIG. 1 illustrates a schematic perspective view of the patient positioner article of manufacture, apparatus, system, kit and method in accordance with an embodiment of the present invention.

Non-limiting embodiments of the present invention will be described below with reference to the accompanying drawings, wherein like reference numerals represent like elements throughout. While the invention has been described in detail with respect to the preferred embodiments thereof, it will be appreciated that upon reading and understanding of the foregoing, certain variations to the preferred embodiments will become apparent, which variations are nonetheless within the spirit and scope of the invention.

The terms "a" or "an", as used herein, are defined as one or as more than one. The term "plurality", as used herein, is defined as two or as more than two. The term "another", as used herein, is defined as at least a second or more. The terms "including" and/or "having", as used herein, are defined as comprising (i.e., open language). The term "coupled", as used herein, is defined as connected, although not necessarily directly, and not necessarily mechanically.

Reference throughout this document to "some embodiments", "one embodiment", "certain embodiments", and "an embodiment" or similar terms means that a particular feature, structure, or characteristic described in connection with the embodiment is included in at least one embodiment of the present invention. Thus, the appearances of such phrases or in various places throughout this specification are not necessarily all referring to the same embodiment. Furthermore, the particular features, structures, or characteristics may be combined in any suitable manner in one or more embodiments without limitation.

The term "or" as used herein is to be interpreted as an inclusive or meaning any one or any combination. Therefore, "A, B or C" means any of the following: "A; B; C; A and B; A and C; B and C; A, B and C". An exception to this definition will occur only when a combination of elements, functions, steps or acts are in some way inherently mutually exclusive.

The drawings featured in the figures are provided for the purposes of illustrating some embodiments of the present invention, and are not to be considered as limitations thereto. The term "means" preceding a present participle of an operation indicates a desired function for which there is one or more embodiments, i.e., one or more methods, devices, or apparatuses for achieving the desired function and that one skilled in the art could select from these or their equivalent in view of the disclosure herein and use of the term "means" is not intended to be limiting.

The term "body" refers to a physical structure of a human being (or animal) comprising a torso with a right side, a left side, a front side, a back side and not including the head, limbs such as arms, legs or thighs. The term "limb" refers to a physical structure of a human being (or animal) comprising arms, legs and thighs.

The term "surgical operation" or "medical procedure" means a medical procedure on a patient or human being. In some surgical operations, a patient may be placed on a support table which is oriented horizontally and otherwise perpendicular respect to the vertical orientation. However, depending on the medical procedure, it may be more advantageous to orient the patient at an incline with respect to the horizontal by tilting the support table or Table. The term "incline" refers to orienting the patient relative to the plane of the OR Table such as, for example, the body of the patient may be tilted at an angle with respect to the horizontal, such that: the head of the patient is disposed lower than the body (e.g. Trendelenburg position); the head of the patient is disposed higher than the body (e.g. reverse Trendelenburg position and/or Fowler's position); the right side of the patient is disposed higher than the left side of the patient; the left side of the patient is disposed higher than the right side of the patient; or a combination of any of the foregoing.

The term "hook" "hook fabric" "hook foam" "hook material" or "loop" "loop fabric" "loop foam" "loop material" means a fastening device and/or system to operably connect hooks and loops together such as, for example, VELCRO® brand fabric, tape or segments described in U.S. Pat. No. 3,009,235 and currently manufactured by Velcro Industries B.V.

As is illustrated in FIGS. 1 through 16A-16E, the patient positioner 100 refers to an article of manufacture, kit, assembly, system, and method of a positioning a patient useful in surgical procedures to secure and hold a patient on a support table or Operating Room (OR) table 101. According to an embodiment of the patient positioner 100 as shown in FIG. 1, the system 100 used on the support table 101 comprises a sheet assembly 110, a pad assembly 120 that includes a film 130 (for protecting a patient-facing surface of the pad assembly 120), and may further include instructions or safety placards 131 for the safe use thereof. The system 100 further comprises a support table pad 140 having hook portions 146 configured to operably connect to a loop base 117 of the sheet assembly 110 operably connecting the support table pad to the sheet assembly 110. The sheet assembly 110 can be configured as a cover, commonly termed a sheet and/or drape, from suitable materials impermeable or otherwise that do not permit the passage of a fluid through its substance to the table pad 140 or the split-pad assembly 150, 160.

Figure 15:
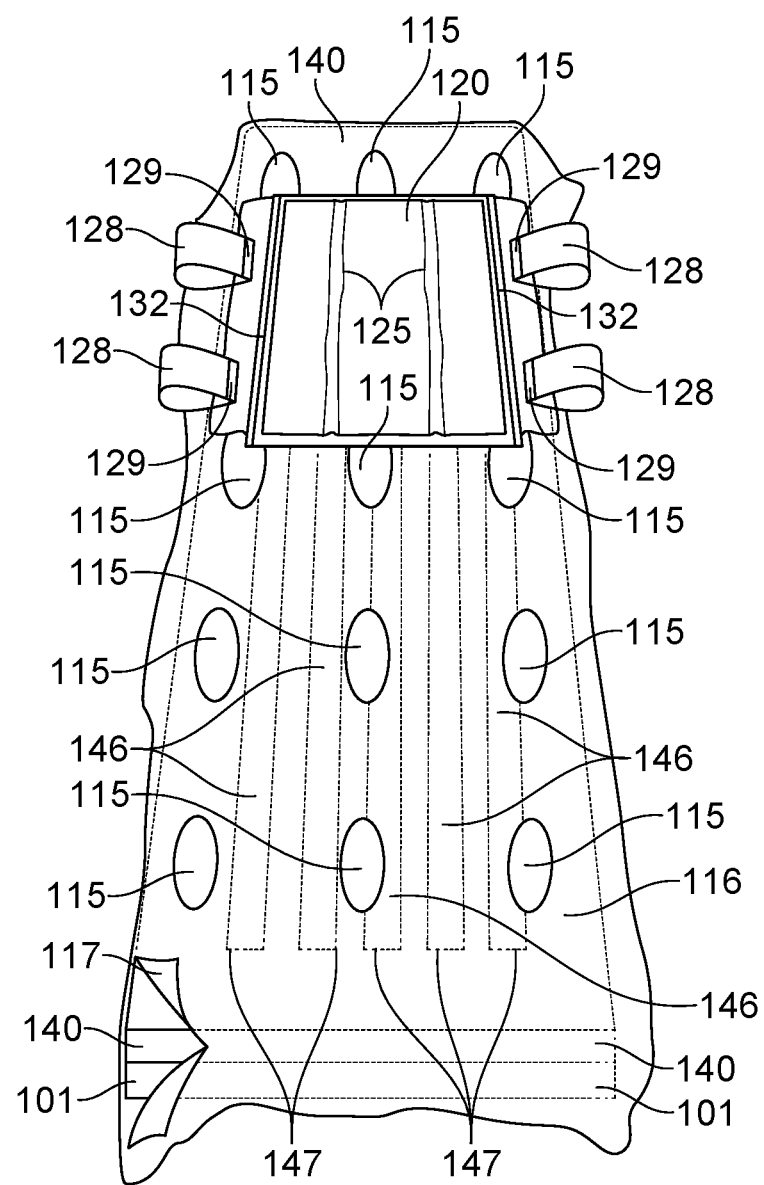
FIG. 15 is a schematic perspective top view of the environment of the patient positioner disposed support table pad according to an embodiment of the present invention.
Figure 16A:
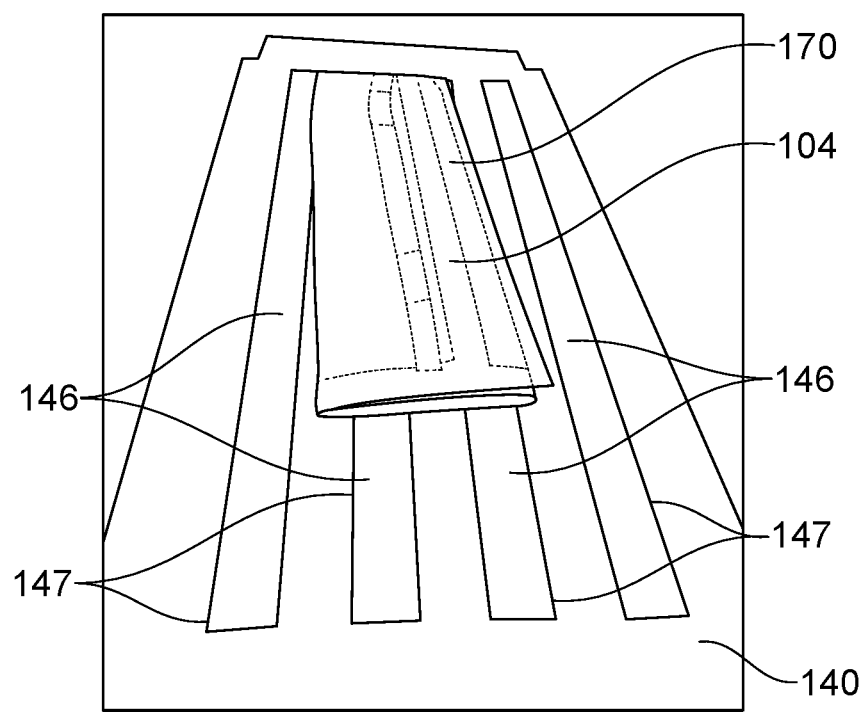
FIGS. 16A-16E are schematic views of the method for patient positioning using a positioner assembly, system, article of manufacture, and kit according to an embodiment of the present invention.
Figure 16B:
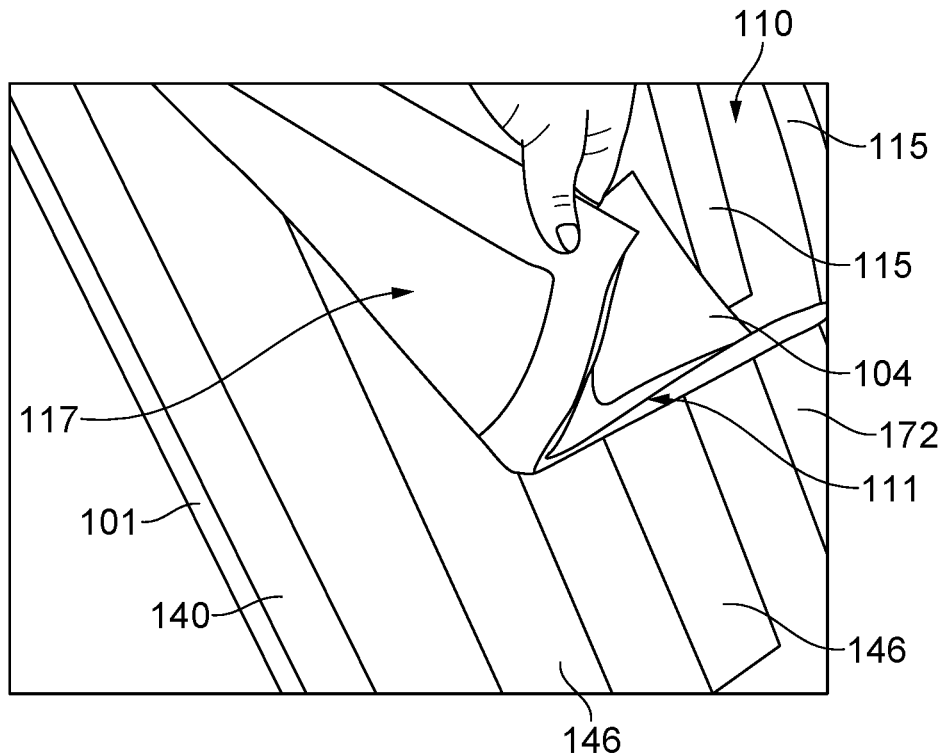

The pad assembly 120 can operably connect to the to hook portions 115 formed on the sheet assembly 110 using one or more loops 126 that may be formed in strips or sheets, as loop fabric, a loop foam, or other loop fastener as shown in FIGS. 1-4. One or more double-sided loop portions 127 may operably connect to the hook portions 115 formed on the sheet assembly 110 and the double-sided loop portions 127 are configured to operably connect one or more limb or arm straps 128 having a hook portion and/or double-sided hook portion 129 on the ends thereof as shown in FIGS. 15 and 16A-16B. In this manner the pad assembly may be secured to the patient so as to operably connect the patient to the support table 101 for the surgical procedure.

According to an embodiment of the patient positioner 100 comprises a table pad 140 having hook portions 146 to operably connects to the loop base sheet 117 of the sheet assembly 110, as shown in FIGS. 1 and 6-9. According to another embodiment of the patient positioner 100 a support table split-pad assembly 150 is useful when removal of a portion of the pad is desired as shown in FIGS. 10-14. The support table split-pad assembly 150 comprises a pad body 151 and a second pad 160 that support table split-pad assembly 150 operably connects to the sheet assembly 110 via the loop base sheet 117 as described herein.

The patient positioner 100 is useful in the environment of general and special surgical procedures using a support table 101. Sheet assembly 110 forms a reusable cover that covers the table pad 140 or support table split-pad assembly 150 connected to the support table 101. In this manner, sheet assembly 110 may be removed between each surgical procedure. The table pad 140 or split-pad assembly 150 is manufactured from suitable, durable materials so as to be cleaned between each use.

The patient positioner 100 using the sheet assembly 110 is configured to provide a barrier to fluids advancing through the barrier to the table pad 140, 150 of a support table 101. The sheet assembly 110 advantageously may be used on a variety of configurations of a support table 101 in multiple environments such as, for example, the support table pad 140 embodiment, or the split-pad assembly 150. The pad assembly 120 can be located on the sheet assembly 110 in a desired position operably connecting the hook portions 115 to the loop fabric 126, and the patient can be positioned on the film 130 and pad assembly 120. The film 130 may be removed to expose the upper portion 122 and channels 125 for application to the body of the patient, for example, the patient may be rolled on one side or another, or both, to remove the film 130. If straps 128 are desired to hold a limb and/or arm of the patient, one or more double-sided loop strips 127 on one side are secured to the hook portions 115 of the sheet assembly 110 that also can also be aligned with the gel pad 120, and hook portions 129 on the opposite side of the straps 128 being operably connected to the one or more double-sided loop strips 127. In this manner, the patient positioner 100 secures the patient to the support table 101 so as to hold and maintain a desired patient position (e.g. in Trendelenburg, reverse Trendelenburg and/or Fowler) throughout the surgical procedure.

Referring now to FIGS. 1 and 15, the patient positioner 100 comprises a sheet assembly 110 having a cover 111 that may be formed as a surgical drape and/or sheet having a top portion 112, bottom portion 113, side portions 114, one or more hook portions 115 affixed to the top portion 112 of the cover 111, and a loop base sheet 117 affixed to the bottom portion 113. The sheet assembly 110 may form a surgical drape and/or sheet of a single and/or multiple layer construction, e.g. suitable materials and constructions that complies with Spunbond-Meltblown-Spunbond (SMS) healthcare material standards. Loop base sheet 117 may be formed from a section of loop fabric and may operably connect the sheet assembly 110 to the table pad 140, and/or the split-pad assembly 150. Loop base 117 may be oriented to align and join with the hook portions 146 on table pad 140 or split-pad assembly 150. The cover 111 can have loops 117 formed on the bottom portion 113 by bonding and other manufacturing techniques.

As shown in FIGS. 1, 5 15 and 16A-16E, the hooks 115 can be formed in one or more predetermined locations, shapes and/or orientations. For example, each of the one or more hook portions 115 may take any form and vary in shape and size such as uniform, variable-sized segments, linear strips, sheets, oval, or circular portions affixed to the cover 111 such as, for example, uniform segments, variable-sized segments, elongated linear strips, square portions, rectangular portions, oval portions, and circular portions Similarly, the predetermined location(s) of hook portions 115 may vary according to the orientation that best serves the purpose of maintaining a desired patient position for a particular surgical procedure. Furthermore, hook portions 115 may be ultrasonically bonded to the cover 111 at said predetermined locations. According to the present invention, one or more hooks, hook segments and/or hook portions 146 may be integrally formed in the upper and/or lower portions 143, 144 of the support table pad 140 and/or split-pad 150, by forming the one or more hook portions 115 in the top portion 112 of the sheet assembly 110, or other loop engaging structures affixed to by ultrasonic manufacturing techniques.

The sheet assembly 110 of the patient positioner 100 is configured with the hook portions 115 positioned to join with the loop fabric 126 and/or double-sided loop portions 127 for use in holding and securing the patient torso and arms. For example, the cover 111 has hook portions 115 formed by manufacturing techniques of bonding hooks to the surfaces of the cover 111 and the bed cover portion 142, 153 and/or 162 wherein such ultrasonically bonding or welded, as opposed to stitched seams, so as to prevent fluid penetration through the bed cover portion 142, 153 and 162 to the bed body 141, 151 and 161. Moreover, the bed cover portion 142, 153 and/or 162 is made durable to extend the use of the table pad 140, or 150, 160. The bed cover portion 142, 153 and/or 162 are configured to be cleanable between surgical procedures whereby the sheet assembly 110 and pad assembly 120 can be sterilized and disposed of after each surgical procedure.

Referring to FIGS. 1-4, the pad assembly 120 comprises a gel body 121 having an upper portion 122, a lower portion 123, and side portions 124. The gel body 121 may be formed with channels 125, suitable flexible, cushioning and/or semi-solid materials including a foam, a closed-cell foam, phase-4 gel, a gel material suitable to operably connect to the patient. For example, the one or more channels 125 may be formed within the upper portion 122 of the gel body 121. Loop fabric 126 is affixed or otherwise securely connected to the lower portion 123 of the gel body 121. The loop fabric 126 can comprise a sheet with an upper surface and a lower surface. The one or more loops may be formed on the lower surface and/or upper surface, or both as in a double-sided loop fabric wherein the side portion 127 are integrated and extend outwardly from the gel body 121. Consequently, the loop fabric 126 may be formed in strips or sheets, and adhered to the gel body 121 by a direct bonding to a loop fabric sheet, e.g. forming by bonding a gel directly to the loop fabric, single and/or double-sided, to form a semi-solid gel body 121 having the channels 125. Similarly, the gel body 121 may be secured to a loop foam sheet 126a and adhered to the gel body 121 by a direct bonding to a loop foam sheet 126a. According to another embodiment of the present invention, the one or more loop, loop segments, loop portions, and/or or other loop engaging structures. may be manufactured in a unitary construction with the top and/or bottom portions 112, 113, respectively, of sheet assembly 110, loop sheet 126 of the pad assembly 120, and one or more double-sided loop portions 127 may be secured on either side of the pad assembly 120 or other suitable configuration to operably connect to hook portions 129 disposed on at least one end of the one or more limb and/or arm straps 128, for example, so as to hold the arms of the patient undergoing the surgical procedure.

Figure 2:
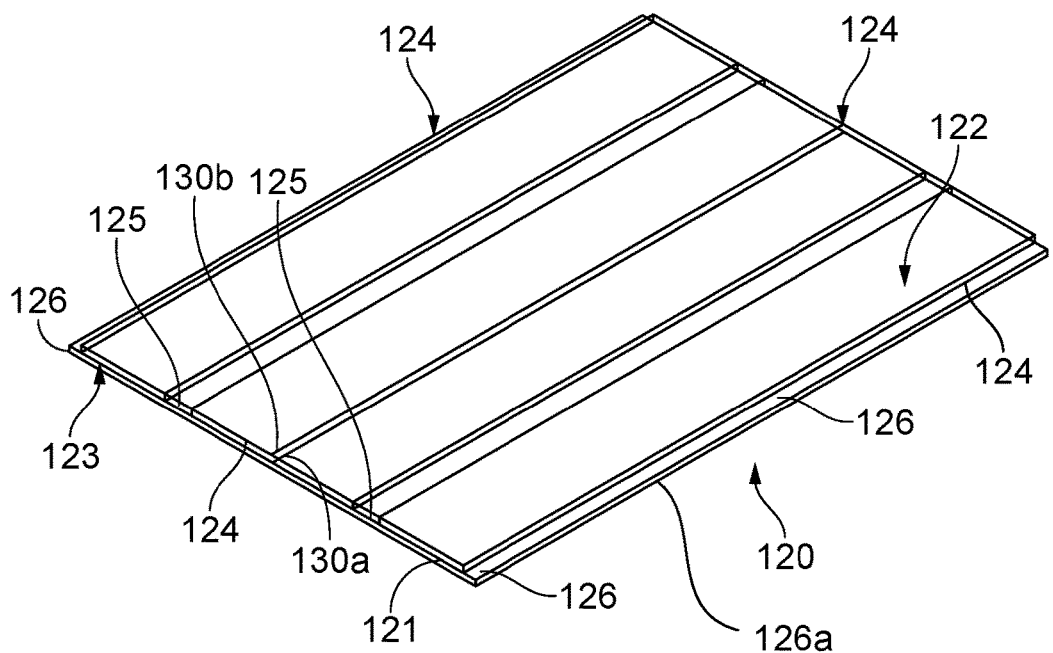
FIG. 2 illustrates a schematic perspective view of a pad assembly according to an embodiment of the present invention.
Figure 3:
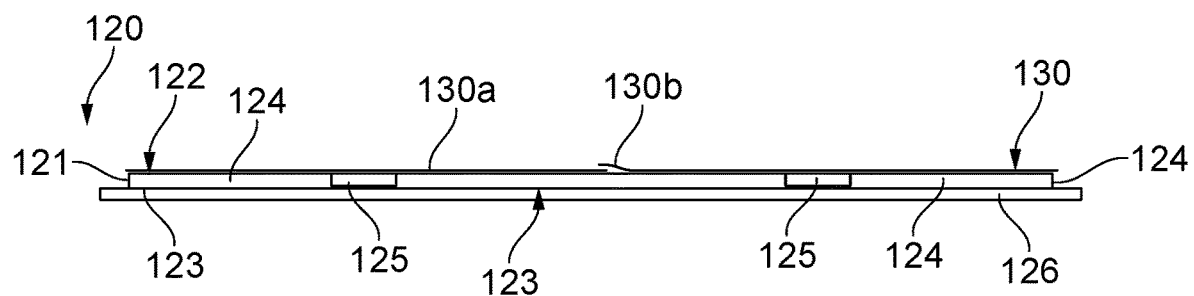
FIG. 3 illustrates an end view of the pad assembly.
Figure 4:
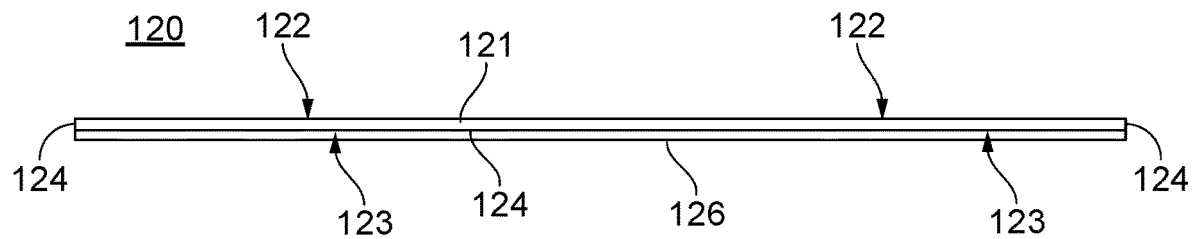
FIG. 4 illustrates a side view of the pad assembly.
Figure 5:
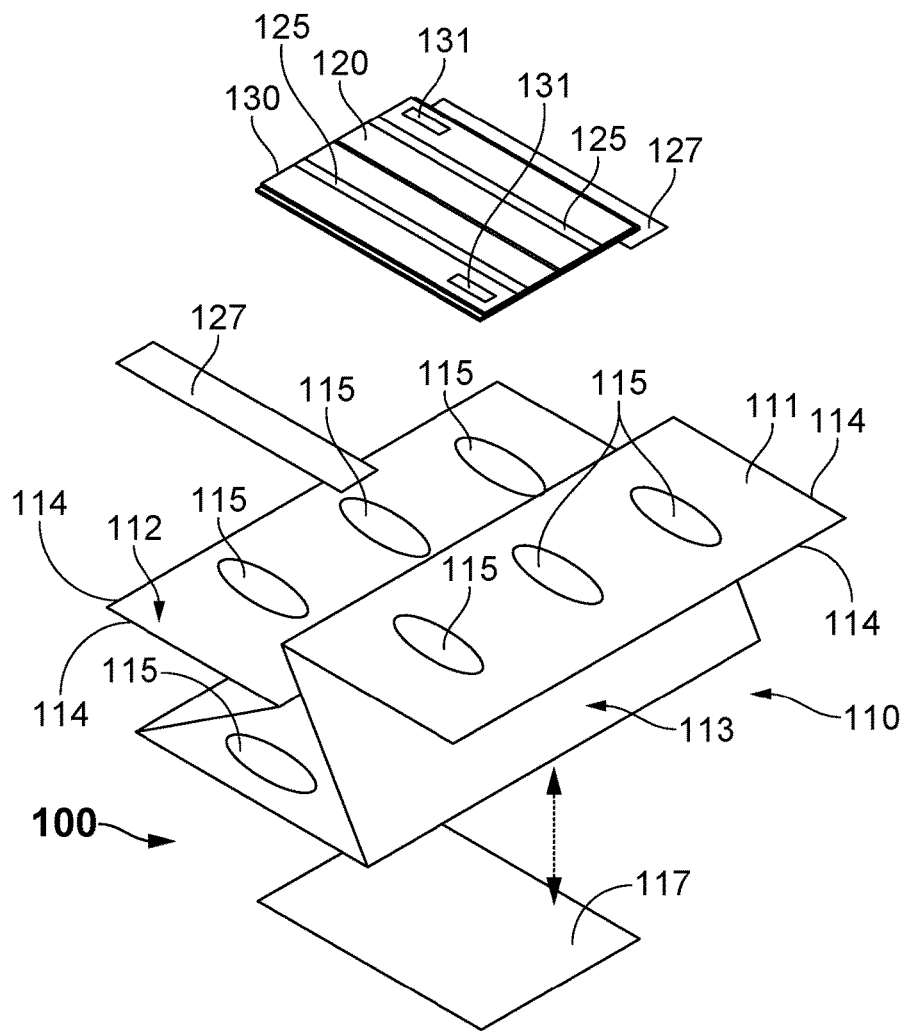
FIG. 5 is a schematic view of article of manufacture, kit, and patient positioner system.
Figure 6:
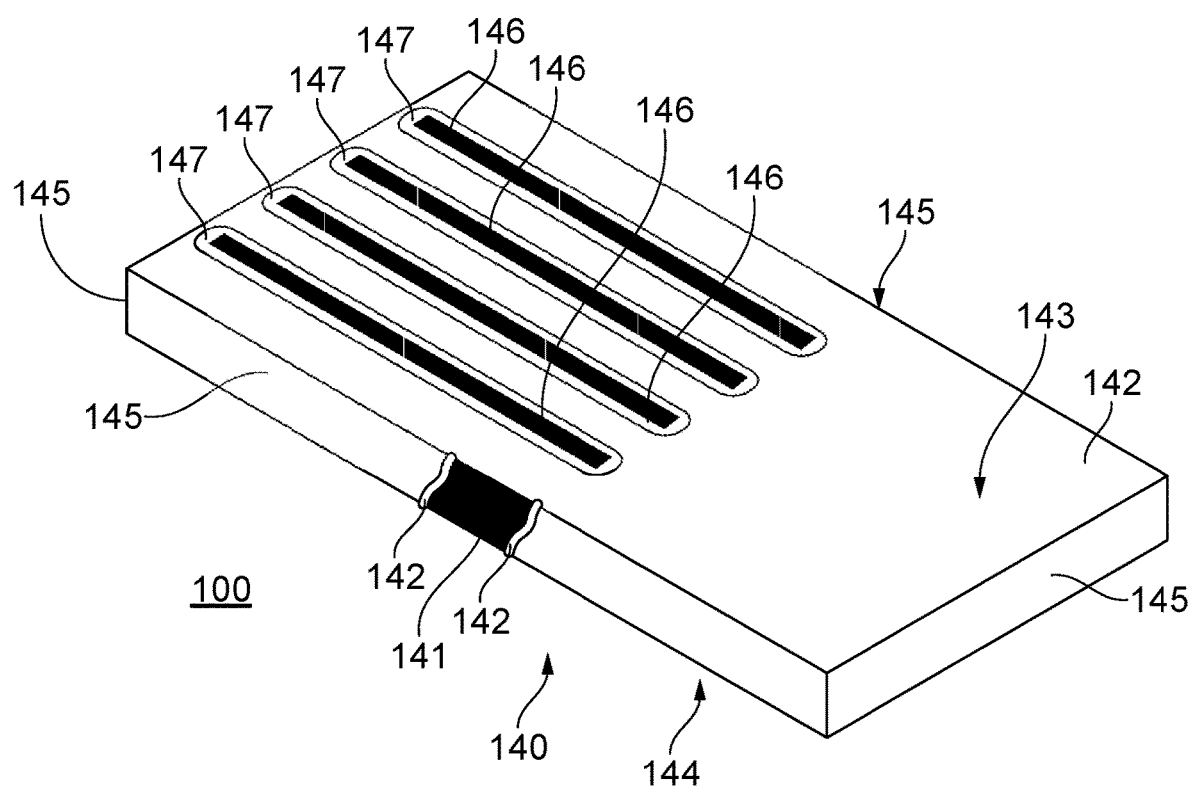
FIG. 6 is a schematic top perspective view of a support table pad according to an embodiment of the present invention.
Figure 7:
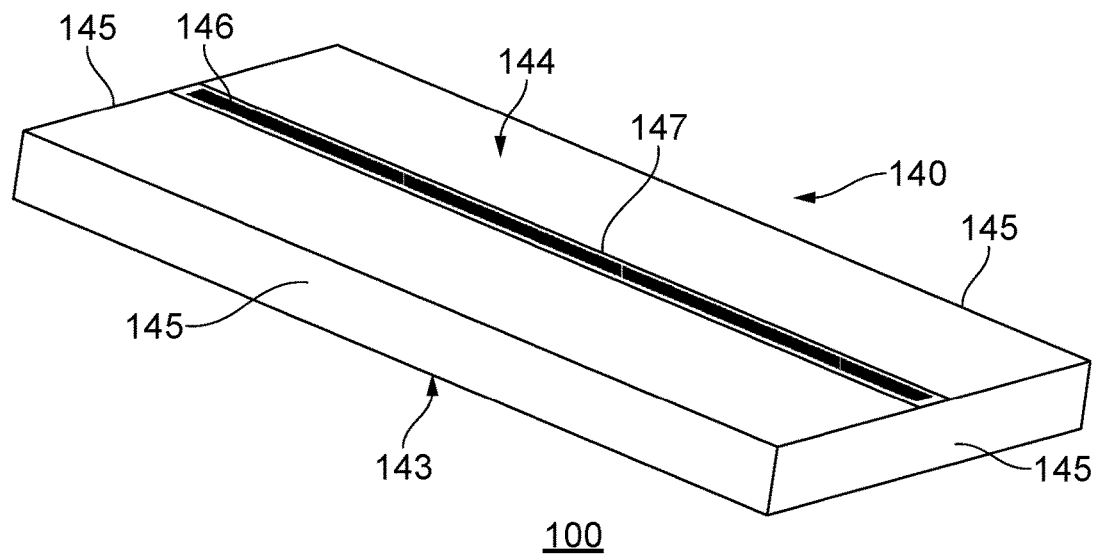
FIG. 7 is a schematic bottom perspective view of a support table pad according to an embodiment of the present invention.
Figure 8:
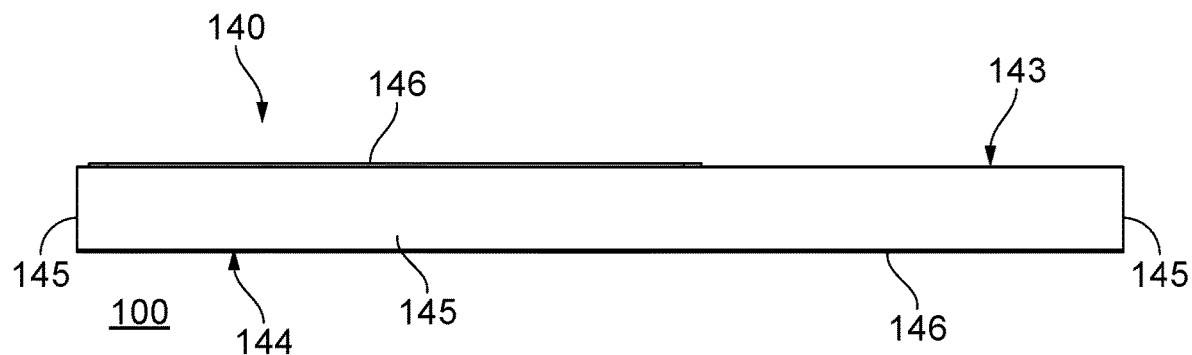
FIG. 8 is a schematic side view of the support table pad thereof.
Figure 9:
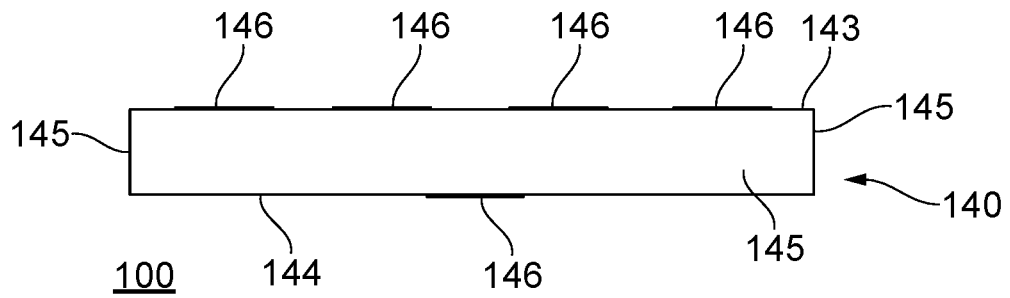
FIG. 9 is a schematic end view of the support table pad thereof.
Figure 10:
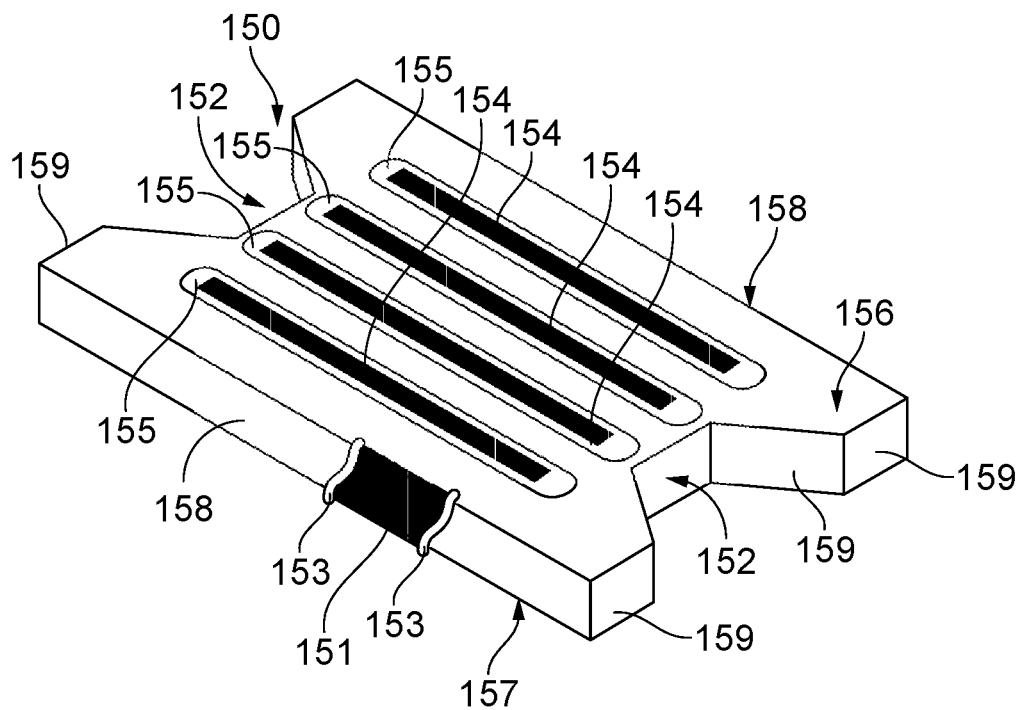
FIG. 10 is a schematic top perspective view of a support table pad according to another embodiment of the present invention.
Figure 11:
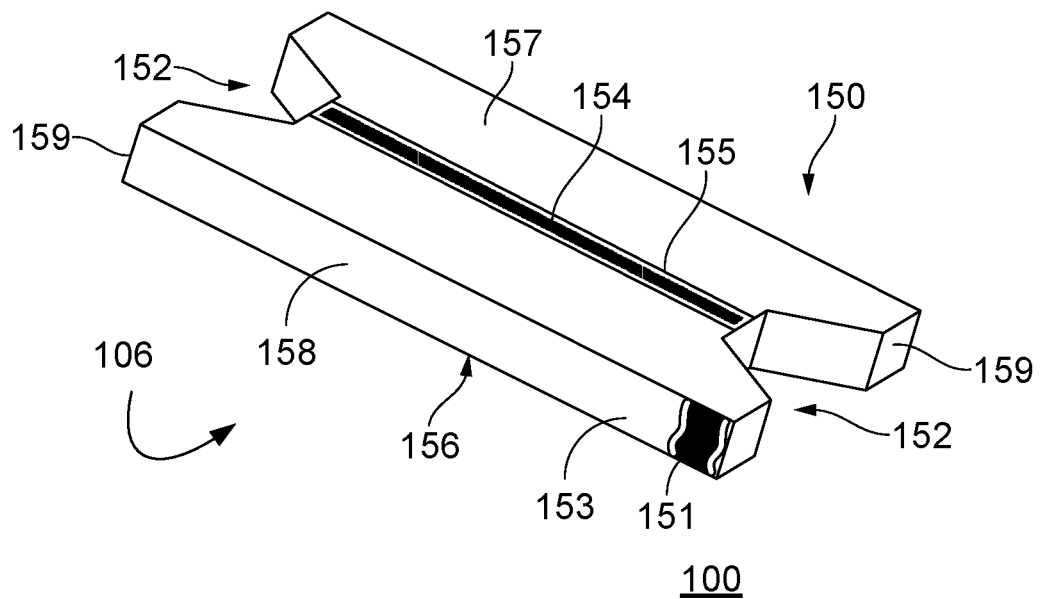
FIG. 11 is a schematic bottom perspective view of a first segment of a support table pad according to an embodiment of the present invention.

As shown in FIGS. 1-3, the film 130 also may be formed in one or more portions, such as first portion 130a and second portion 130b to assist in application. A placard 131 can be affixed or printed on the film 130 for instructions on proper use, safety, and/or other information to the user. The film 130 is manufactured from suitable releasable materials that provides a film that can protect the upper portion 122 and one or more channel 124 of the pad assembly 120. The film 130 may be manufactured from suitable materials and plastics to release as desired so as to apply to the upper portion on the body of the patient, e.g. remove film 130 to place the pad assembly 120 on the patient thereby being useful for operably connecting the pad assembly 120 to the patient's body such as, for example, body, torso, limb, appendage, and/or skin.

In another embodiment, one or more loop strips 127, shown as loop strip 127a and 127b, may be secured on either side of the pad assembly 120 or other suitable configuration to hold a body part, e.g. each arm of a patient. For example, the patient positioner 110 may include straps to hold the patient's limbs that have hook portions 129 on an end thereof, whereby patient positioner 110 can include one or more double-sided loop strips 127 for engaging hook portions 115 on the cover 111 of the sheet assembly and hook portions 129 on an end of the strap 128, e.g. arm and/or limb straps.

As shown in FIGS. 6-9, the patient positioner 100 further comprises a table pad 140 having a bed body 141, a bed cover 142 having a top portion 143, a bottom portion 144, and side portions 145. The bed body 141 of the table pad 140 can be manufactured from suitable materials including 1.5" thick soft foam that conforms to body contours for a custom fit. The bed cover 142 comprises embedded hook portions 146 adhered to top portion 143 to connect to the loop fabric 117 of the sheet assembly 110. Similarly, the bed cover 142 may include embedded hook portions 147 adhered to bottom portion 144 for operably connecting to loops or other means used to secure the table pad 140 to the support table 101. These hook portions 146 and 147 may be formed using machines or techniques to maintain a barrier between the bed cover 142 and the bed body 141.

As shown in FIGS. 10-14, the patient positioner 100 further comprises another embodiment of a split-pad assembly 150 comprising a pad body 151 having at least one notch 152 and a second pad 160 having a body 161 with a protrusion 167 configured to engage the notch 152. The pad body 151 can be configured with a top portion 156, a bottom portion 157, and side portions 158. The pad body 151 comprises the notch 152 formed therein on one or more side portions 158 and/or end portions 159 and a bed cover 153 having hook portions 154 formed on an upper portion 156 and/or a lower portion 157 therein by machine, adhesive, welding or other ultrasonic bonding techniques. The pad body 151 of the table pad 150 can be manufactured from suitable materials including 1.5" thick soft foam that conforms to body contours for a custom fit. The bed cover 153 comprises embedded hook portions 154 adhered to top portion 156 to connect to the loop fabric 117 of the sheet assembly 110. Similarly, the bed cover 153 may include embedded hook portions 154 adhered to bottom portion 157 for operably connecting to loops or other means used to secure the table pad 150 to the support table 101. These hook portions 154 may be formed in elongated strips or other placement configurations using machines or techniques to maintain a barrier between the bed cover 153 and the pad body 151.

Figure 12:
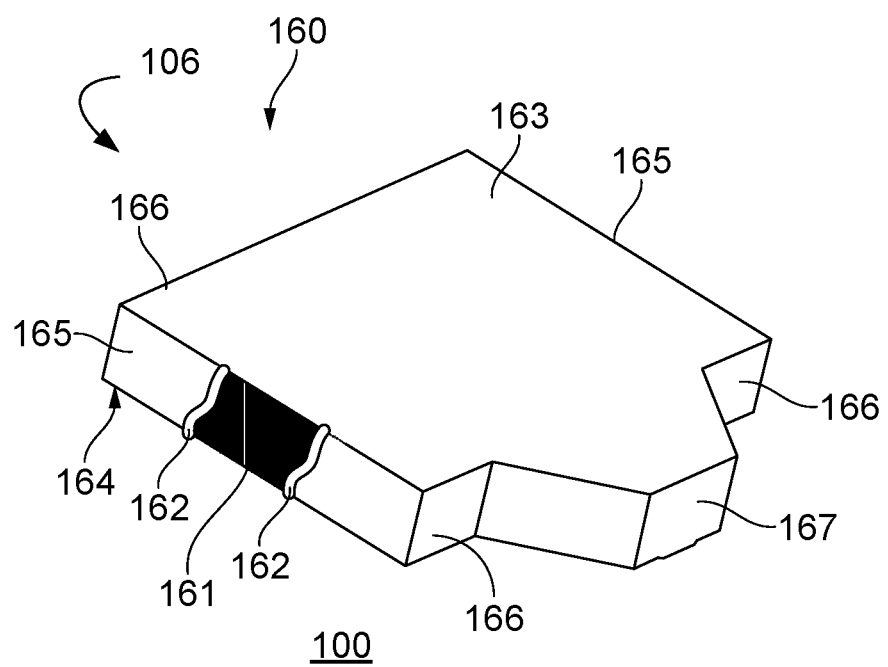
FIG. 12 is a schematic top perspective view of a second support table pad for operatively conforming to the first segment of a support table pad according to yet another embodiment of the present invention.
Figure 13:
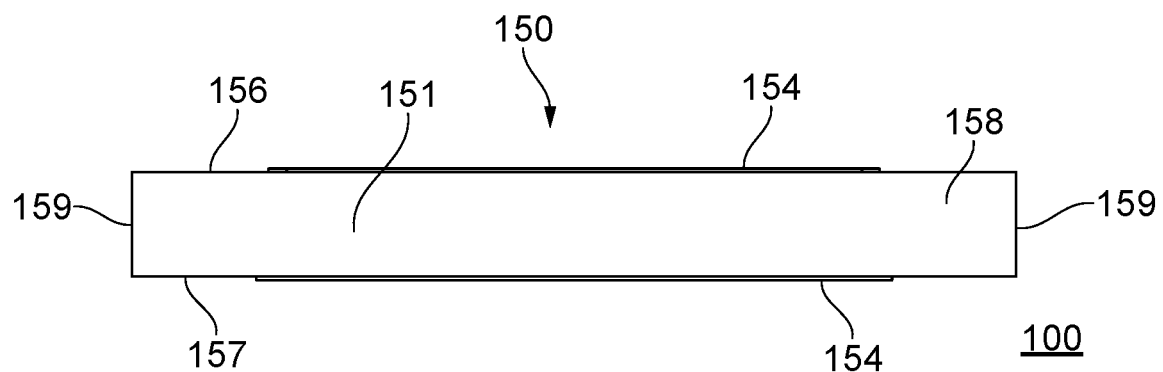
FIG. 13 is a schematic side view of the support table pad thereof.
Figure 14:
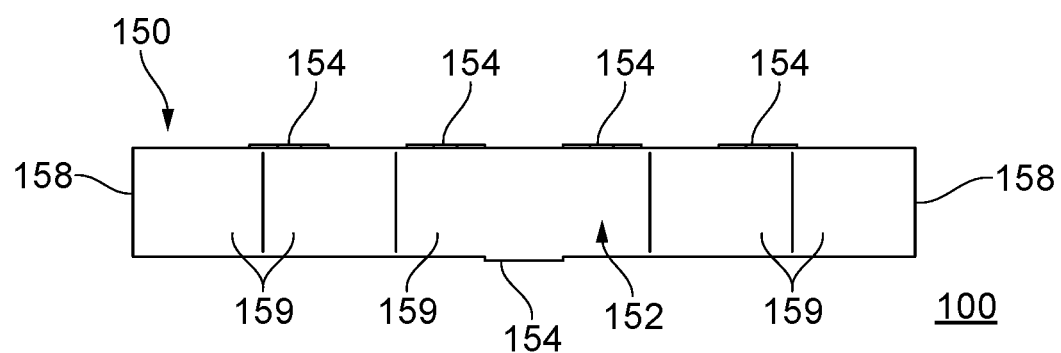
FIG. 14 is a schematic end view of the support table pad thereof.

Referring to FIG. 12, the split-pad assembly 150 comprises a second pad 160 of the patient positioner 100 comprises a body 161, bed cover portion 162, top portion 163, bottom portion 164, side portions 165 and end portions 166 and at least one protrusion 167 on an end 166 thereof. The second pad 160 is useful in supporting the patient for surgical procedures and can be removed during a surgical procedure.

Referring to FIGS. 1, 15 and 16A-16E, the method of assembling the patient positioner 100 on the support table 101 is described according an embodiment of the invention. The patient positioner may be manufactured in bonded layers for the sheet assembly 110 and pad assembly 120. The simplified construction of the patient positioner 100 has advantages of a reduction in steps in a process of assembling on the support table 101 for a surgical procedure. The table pad 140 and/or split-pad assembly 150 is may be fixedly attached to the support table 101, or may be formed integral to the support table 101, such that the support table 101 can be inverted such as, for example, by fastening the table pad 140 using hook portions 154 on the lower portion 157 operably connecting to loop portions (not shown) disposed on the support table 101.

Referring to FIG. 16A, the patient positioner 100 can be configured as a sheet kit and/or an article of manufacture 104 comprising a sheet assembly 110, pad assembly 120, one or more double-sided loop portions 127 and straps 128. The sheet kit 104 may be sealed within clear plastic or other container 170 for ease of storage and transport to/from the support table 101 and may include instruction placards 131 disposed on film 130 and/or container 170 that provide written instructions to facilitate preparation of the patient positioner kit for a surgical procedure. The contents of the sheet kit 140 are removed from the container 170 for use in a surgical procedure. As is illustrated in FIGS. 1-9, 15 and 16A-16B, the patient positioner 100 can be configured as a system 105 comprising a support table pad 140 configured to operably connect the kit and/or an article of manufacture 104 to the support table 101. As is illustrated in FIGS. 1-5, 10-14,15 and 16A-16B, the patient positioner 100 can be configured as a split-pad patient positioner system 106 comprising the article of manufacture 104 and a split-pad 150 having a first pad 151 and a second pad 160 configured to operably connect the kit and/or an article of manufacture 104 to the support table 101.

As is illustrated in FIGS. 1-9, 15 and 16A-16E, the operation of the patient positioner 100 is described. The sheet assembly 110 can be formed as a cover 111 configured to cover and/or drape over a table pad 140 and/or split-pad 150 secured to the support table 101, whereby the one or more hook portions 146 operably connect to the loop base sheet 117. Similarly, the loop fabric 126 of pad assembly 120 operably connects to one or more hooks 115 formed in the top portion 112 of cover 111. The pad assembly may be connected to the patient by removal of the film 130 for positioning of a patient for a surgical procedure.

Figure 16C:
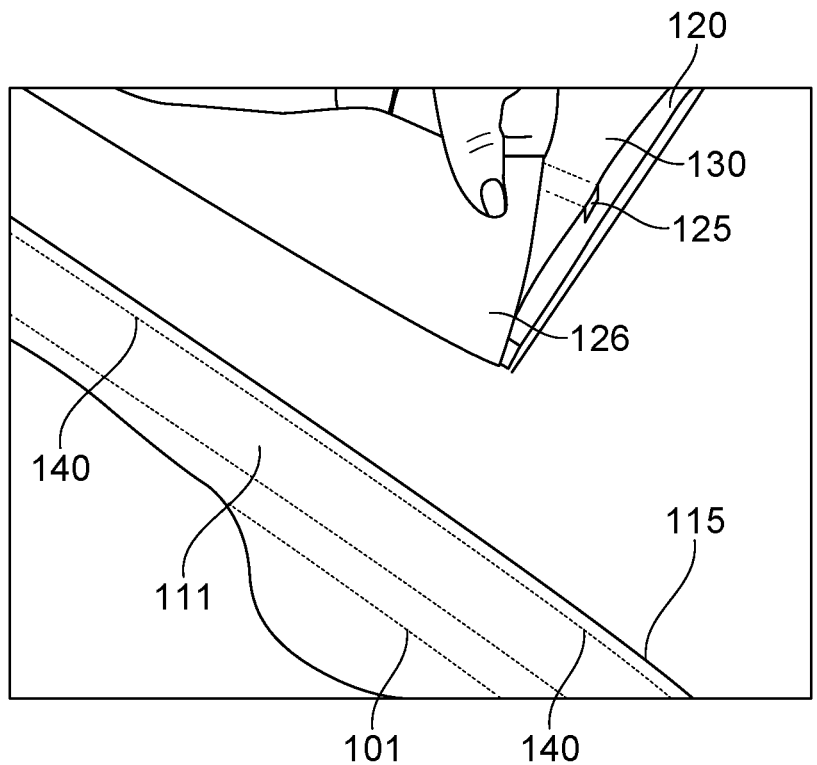
Figure 16D:
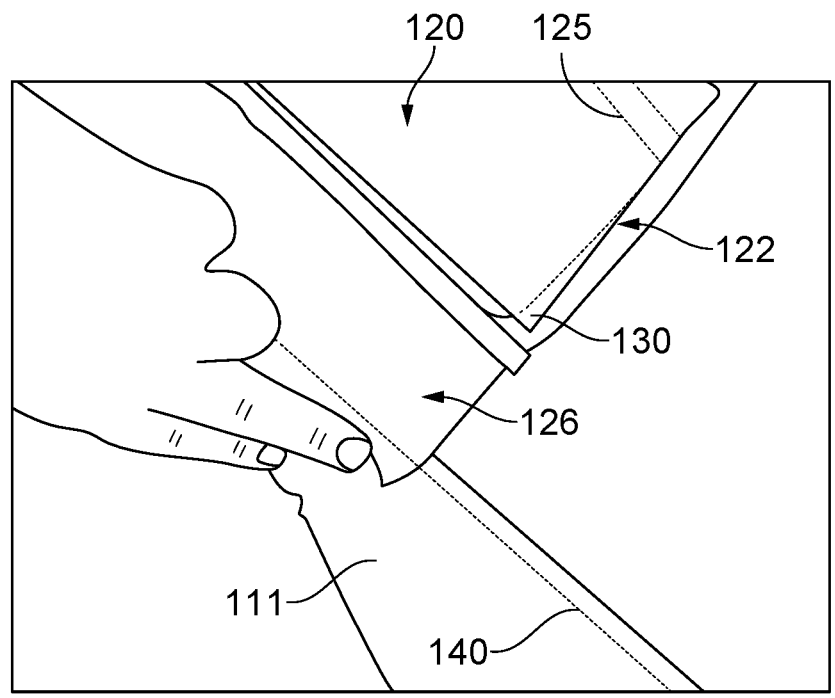
Figure 16E:
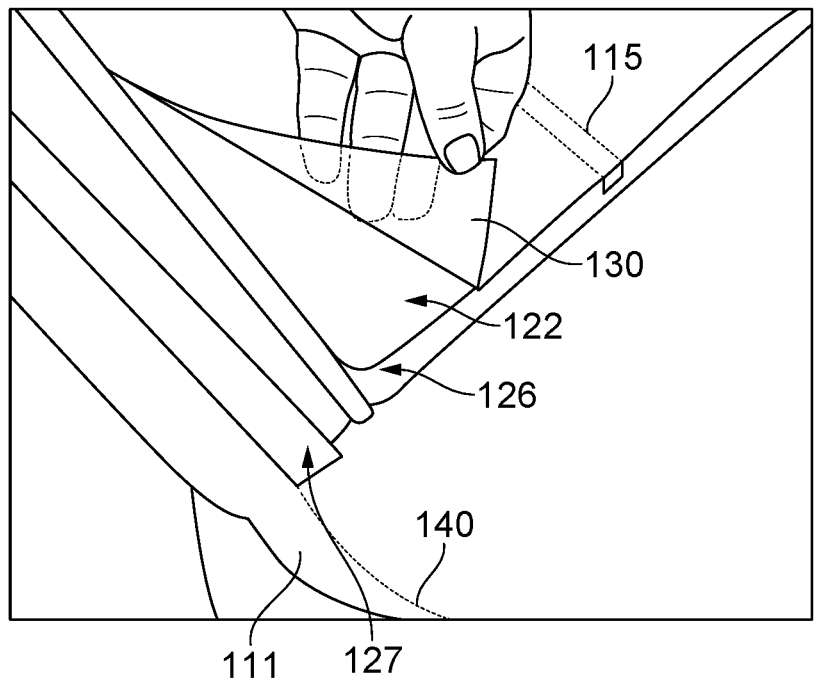

Referring to FIG. 16B, in a Step 1, the sheet assembly 110 may be disposed on table pad 140, or split-pad 150, whereby loop base sheet 117 may be aligned to embedded hook portions 146 and operably connected to the same, such that top portion 112 of cover 111 is positioned generally outward from support table 101. The cover 111 may be fitted over table pad 140 to form a drape covering that may extend beyond side portions 145 of table pad 140, as shown in FIG. 15. In this way, one or more hook portions 115 may be positioned generally outward from OR Table 101. Referring to FIG. 16C, in a Step 2, loop fabric 126 of pad assembly 120 may be aligned to hook portions 115 such that loop fabric 126 operably connects to said hook portions 115. For example, the lower portion 123 of pad assembly 120 may be aligned to loop fabric 126 so that lower portion 123 operably connects to sheet assembly 110. Referring to FIG. 16D, in a Step 3, the one or more double-sided loop portions 127 can be positioned to extend from the side portions 124 of the pad assembly 120 so as to attach the straps 128 by hook portions 129. Referring to FIG. 16E, in a Step 4, the film 130 may be removed so as to operably connect the upper portion 122 to the patient with the one or more channels 125 positioned adjacent the patient. For example, the patient can be placed in the desired position on the pad assembly 120 and rolled to one side such that the film 130 may be removed, thereby exposing the body 122 of pad assembly 120 for operably connecting to a patient. Alternatively, in Step 4, film 130 may be removed and a patient operably connected to gel portion 122 by aligning the patient and operably connecting patient with the pad assembly 120 to sheet assembly 110, as provided in Step 4; or removing the film 130 and connecting the body 122 to the patient and operably connecting the loop sheet 126 to the one or more hook portions 115 of the sheet assembly 110.

While certain configurations of structures have been illustrated for the purposes of presenting the basic structures of the present invention, one of ordinary skill in the art will appreciate that other variations are possible which would still fall within the scope of the appended claims. Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

We claim:

1. A patient positioner system for a support table comprising:
    a table pad comprising a bed body, a bed cover portion enclosing said bed body having an upper portion, a lower portion and side portions, and said bed cover portion having one or more hook portions formed on said upper portion;
    a sheet assembly comprising a sheet having a top portion, a bottom portion and edge portions, said top portion having one or more hook portions formed therein, said bottom portion having a loop fabric, said bottom portion of said sheet configured to operably couple to said one or more hook portions of said upper portion of said bed cover portion; and
    a pad assembly comprising a body and a loop fabric, said body having a lower portion and an upper portion, said upper portion including one or more channels formed therein, said loop fabric being coupled to said lower portion of said body, said loop fabric characterized by loops on said lower surface thereof, said lower portion of said pad assembly configured to operably couple to said one or more hook portions of said top portion of said sheet; and one or more straps having at least one end thereof, said at least one end configured to operatively coupled to said pad assembly and/or said sheet assembly, said one or more straps being adapted to hold a limb of a patient.

2. The patient positioner system of claim 1, said table pad further comprising one or more loop and/or hook portions on said lower portion of said sheet assembly for operably connecting to the support table.

3. The patient positioner system of claim 1, said table pad further comprising a split-pad having a pad body with an upper portion, a lower portion, and at least one notch formed in a side and/or end portion, a bed cover enclosing said pad body, said bed cover being configured with one or more hook portions, and a second pad body having a protrusion to operably connect to said at least said one notch and a bed cover portion for enclosing said second pad body.

4. The patient positioner system of claim 1 wherein at least one of said side portions of said table pad including hook portions formed therein.

5. The patient positioner system of claim 1, said sheet assembly further comprising one or more hook portions having a form selected from the group consisting of uniform segments, variable-sized segments, elongated linear strips, square portions, rectangular portions, oval portions, and circular portions.

6. The patient positioner system of claim 1, said pad assembly further comprising a film disposed on said body covering said one or more channels.

7. The patient positioner system of claim 6 wherein said film including one or more safety placards.

8. The patient positioner system of claim 1 wherein said body of said pad assembly is formed from a material selected from the group consisting of a foam, a closed-cell foam, a phase-4 gel, and a gel.

9. The patient positioner system of claim 1, further comprising one or more double-sided loop portions configured to operably couple said at least one end of said straps to said pad assembly.

10. An article of manufacturing for a support table, comprising:
    a sheet assembly comprising a sheet having a top portion, a bottom portion and edge portions, said top portion having one or more hook portions formed therein, said bottom portion having a loop fabric, said loop fabric of said bottom portion configured to operably couple said sheet assembly to said support table;
    a pad assembly comprising a body portion and a loop fabric, said body portion having an upper portion with one or more channels formed therein, a lower portion being operably coupled to said loop fabric and side portions, and a film disposed on said upper portion, said film configured to cover said upper portion prior to surgery;
    one or more straps having at least one end thereof, said at least one end having a hook portion and/or double-sided hook portion thereon;
    one or more double-sided loop portions configured to operably couple said one or more straps to said loop fabric of said sheet assembly; and.

* * * * *